United States Patent
Datta et al.

(10) Patent No.: US 12,263,024 B2
(45) Date of Patent: Apr. 1, 2025

(54) SYSTEM AND METHOD FOR INCORPORATING LIDAR-BASED TECHNIQUES WITH A COMPUTED TOMOGRAPHY SYSTEM

(71) Applicant: GE Precision Healthcare LLC, Wauwatosa, WI (US)

(72) Inventors: Arka Datta, Pewaukee, WI (US); Brian Edward Nett, Wauwatosa, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 246 days.

(21) Appl. No.: 17/888,642

(22) Filed: Aug. 16, 2022

(65) Prior Publication Data

US 2024/0057955 A1 Feb. 22, 2024

(51) Int. Cl.
| | |
|---|---|
| *A61B 6/03* | (2006.01) |
| *A61B 6/00* | (2024.01) |
| *A61B 6/04* | (2006.01) |
| *A61B 6/58* | (2024.01) |
| *G01N 23/046* | (2018.01) |

(52) U.S. Cl.
CPC .............. *A61B 6/032* (2013.01); *A61B 6/04* (2013.01); *A61B 6/58* (2013.01); *G01N 23/046* (2013.01); *A61B 6/4417* (2013.01); *A61B 6/5205* (2013.01); *G01N 2223/419* (2013.01)

(58) Field of Classification Search
CPC ......... A61B 6/4417; A61B 6/032; A61B 6/04; A61B 6/58; G01N 23/046; G01N 2223/419
See application file for complete search history.

(56) References Cited

U.S. PATENT DOCUMENTS

| | | | | |
|---|---|---|---|---|
| 4,562,540 | A | * 12/1985 | Devaney | G06T 11/006 378/901 |
| 5,966,422 | A | * 10/1999 | Dafni | A61B 6/482 378/15 |
| 7,632,015 | B2 | 12/2009 | Stayman et al. | |
| 8,417,315 | B2 | 4/2013 | Mostafavi et al. | |
| (Continued) | | | | |

OTHER PUBLICATIONS

Li et al., "Augmented Reality-Guided Positioning System for Radiotherapy Patients," Journal of Applied Clinical Medical Physics, 2022, pp. 1-11, Wiley Periodicals.

*Primary Examiner* — Chih-Cheng Kao

(57) ABSTRACT

A medical imaging system includes a CT imaging system including a gantry having a bore, rotatable about an axis of rotation. The CT imaging system includes a table configured to move a subject to be imaged into and out of the bore, a radiation source mounted on the gantry and configured to emit an X-ray beam, and a detector configured to detect the X-ray beam. The medical imaging system includes a LiDAR scanning system physically coupled to the CT imaging system. The LiDAR scanning system is configured to acquire data of the subject from different angular positions relative to the axis of rotation. The medical imaging system includes processing circuitry configured to receive the data acquired with the LiDAR scanning system, to generate a three-dimensional (3D) measurement of the subject, and to utilize the 3D measurement in a subsequent workflow process for a CT scan of the subject.

12 Claims, 15 Drawing Sheets

(56) References Cited

U.S. PATENT DOCUMENTS

| | | |
|---|---|---|
| 8,939,920 B2 | 1/2015 | Maad |
| 10,154,823 B2 | 12/2018 | Von Berg et al. |
| 10,376,217 B2 | 8/2019 | Schmidt et al. |
| 10,712,446 B1 | 7/2020 | Bills et al. |
| 10,737,118 B2 | 8/2020 | Mostafavi |
| 10,823,955 B2 | 11/2020 | Sutton et al. |
| 11,276,166 B2* | 3/2022 | Prasad et al. |
| 2003/0206609 A1* | 11/2003 | Kling .................. G06T 1/20 378/4 |
| 2010/0074497 A1 | 3/2010 | Mielenz |
| 2015/0327831 A1* | 11/2015 | Levin .................. A61B 6/4417 600/407 |
| 2019/0122073 A1 | 4/2019 | Ozdemir et al. |
| 2020/0268333 A1* | 8/2020 | Kenig .................. A61B 6/037 |
| 2021/0110594 A1 | 4/2021 | Teixeira et al. |
| 2021/0251516 A1 | 8/2021 | Pai et al. |
| 2021/0353244 A1 | 11/2021 | Kiely |
| 2021/0373160 A1 | 12/2021 | Kalscheur |
| 2022/0015710 A1 | 1/2022 | Lewis et al. |

\* cited by examiner ically, regular-two dimensional (2D) images obtained with a regular camera cannot produce 3D information. A 3D scout (e.g., acquired utilizing a radiation dose lower than typically utilized during a CT imaging scan used to acquire diagnostic information) may address this issue but with the expense of an additional dose.

SYSTEM AND METHOD FOR INCORPORATING LIDAR-BASED TECHNIQUES WITH A COMPUTED TOMOGRAPHY SYSTEM

BACKGROUND

The subject matter disclosed herein relates to medical imaging systems and, more particularly, to incorporation of light detection and ranging (LiDAR)-based techniques with a computed tomography (CT) imaging system.

In CT, X-ray radiation spans a subject of interest, such as a human patient, and a portion of the radiation impacts a detector where the image data is collected. In digital X-ray systems a photodetector produces signals representative of the amount or intensity of radiation impacting discrete pixel regions of a detector surface. The signals may then be processed to generate an image that may be displayed for review. In the images produced by such systems, it may be possible to identify and examine the internal structures and organs within a patient's body. In CT systems a detector array, including a series of detector elements or sensors, produces similar signals through various positions as a gantry is displaced around a patient, allowing volumetric reconstructions to be obtained.

An accurate three-dimensional (3D) measurement of a patient before or during a CT can significantly improve subsequent workflow (e.g., patient positioning, automated landmarking, etc.). Currently, regular-two dimensional (2D) images obtained with a regular camera cannot produce 3D information. A 3D scout (e.g., acquired utilizing a radiation dose lower than typically utilized during a CT imaging scan used to acquire diagnostic information) may address this issue but with the expense of an additional dose.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In one embodiment, a medical imaging system is provided. The medical imaging system includes a CT imaging system. The CT imaging system includes a gantry having a bore, rotatable about an axis of rotation. The CT imaging system also includes a table configured to move a subject to be imaged into and out of the bore of the gantry, a radiation source mounted on the gantry and configured to emit an X-ray beam, and a detector configured to detect the X-ray beam emitted by the radiation source. The medical imaging system also includes a LiDAR scanning system physically coupled to the CT imaging system. The LiDAR scanning system is configured to acquire data of the subject from different angular positions relative to the axis of rotation. The medical imaging system further includes processing circuitry configured to receive the data acquired with the LiDAR scanning system, to generate a three-dimensional (3D) measurement of the subject, and to utilize the 3D measurement in a subsequent workflow process for a CT scan of the subject with the CT imaging system.

In another embodiment, a CT imaging system is provided. The CT imaging system includes a gantry housing and a gantry coupled to the gantry housing and having a bore, rotatable about an axis of rotation. The CT imaging system also includes a table configured to move a subject to be imaged into and out of the bore of the gantry, a radiation source mounted on the gantry and configured to emit an X-ray beam, and a detector configured to detect the X-ray beam emitted by the radiation source. The CT imaging system includes a LiDAR scanning system. The LiDAR scanning system includes one or more LiDAR scanners configured to acquire data of the subject from different angular positions relative to the axis of rotation. The LiDAR scanning system also includes a guide rail system configured to move one or more LiDAR scanners relative to the gantry. The CT imaging system even further includes processing circuitry configured to receive the data acquired with the LiDAR scanning system, to generate a three-dimensional (3D) measurement of the subject, and to utilize the 3D measurement in a subsequent workflow process for a CT scan of the subject with the CT imaging system.

In a further embodiment, a medical imaging system is provided. The medical imaging system includes a CT imaging system. The CT imaging system includes a gantry housing and a gantry coupled to the gantry housing and having a bore, rotatable about an axis of rotation. The CT imaging system also includes a table configured to move a subject to be imaged into and out of the bore for the gantry, a radiation source mounted on the gantry and configured to emit an X-ray beam, and a detector configured to detect the X-ray beam emitted by the radiation source. The medical imaging system also includes a LiDAR scanning system configured to acquire data of the subject from different angular positions relative to the axis of rotation. The gantry housing includes both a scan window and a LiDAR window disposed about the bore. The one or more LiDAR scanners are disposed beneath the LiDAR window between the scan window and a side of the gantry housing facing the table. The medical imaging system further includes processing circuitry configured to receive the data acquired with the LiDAR scanning system, to generate a three-dimensional (3D) measurement of the subject, and to utilize the 3D measurement in a subsequent workflow process for a CT scan of the subject with the CT imaging system.

BRIEF DESCRIPTION OF THE DRAWINGS

These and other features, aspects, and advantages of the present disclosed subject matter will become better understood when the following detailed description is read with reference to the accompanying drawings in which like characters represent like parts throughout the drawings, wherein.

DETAILED DESCRIPTION

Figure 1:
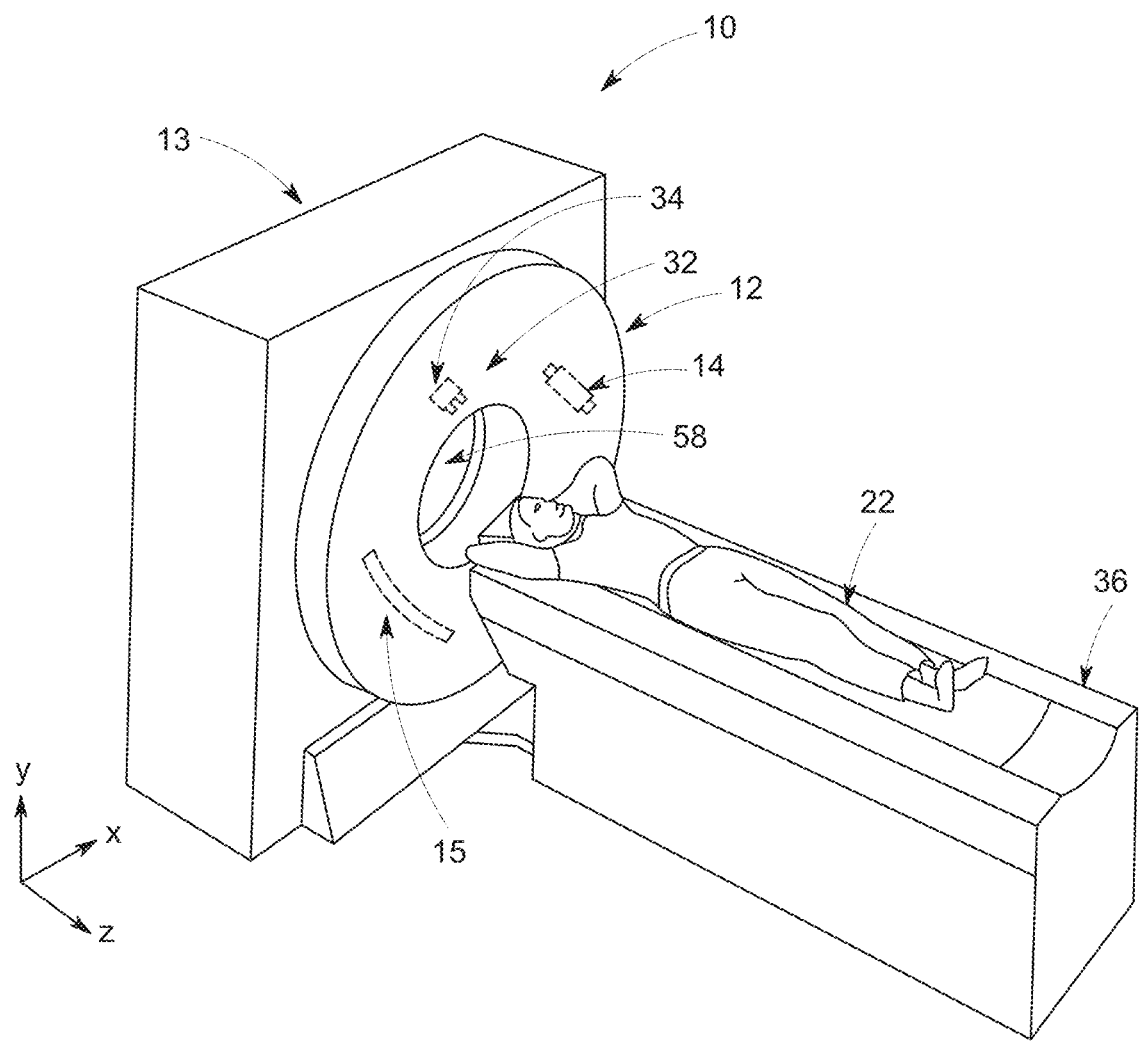
FIG. 1 is a pictorial representation of a CT imaging system, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion may be provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as tomographic image reconstruction for industrial Computed Tomography (CT) used in non-destructive inspection of manufactured parts or goods (i.e., quality control or quality review applications), and/or the non-invasive inspection of packages, boxes, luggage, and so forth (i.e., security or screening applications). In general, the present approaches may be useful in any imaging or screening context to provide accurate 3D information of a target to improving workflow processes and post processing steps.

The present disclosure provides systems and methods for incorporating LiDAR based techniques with a CT imaging system to aid various workflows more efficiently. A LiDAR system is a remote sensing method to measure target objects a variable distance from a source. With the advancement of LiDAR technique, it can now produce 3D rendering of a subject with high spatial resolution (e.g., sub millimeter (mm) accuracy). The disclosed techniques do not need any X-ray radiation to image the target or patient and only require time of flight information of reflected pulsed light (e.g., laser) to calculate and reproduce 3D information (e.g., depth dependent information) of the patient. Multiple views are utilized to cover an entire target area to reproduce high fidelity 3D information. In certain embodiments, light images may be acquired by moving the data acquisition system (i.e., LiDAR scanning system having one or more LiDAR scanners or instruments) across the target (e.g., along the gantry). In this embodiment, the data acquisition system may be integrated outside the scan window (and, thus, physically coupled to the CT system) and rotated to capture multiple views. In certain embodiments, multiple LiDAR scanners or instruments may be placed across different angular positions around the patient to capture the entire region of interest. In certain embodiments, a LiDAR scanning system (e.g., having multiple LiDAR scanners or instruments) may be mounted externally relative to the gantry (e.g., on the scanner housing or the CT table) but still be physically coupled to the CT system. The external LiDAR scanning system may be place in position as required by a guided rail system. The LiDAR-based data may be acquired prior to, during, and subsequent to a CT scan of the target or patient. The LiDAR-based data can be processed and utilized for subsequent (i.e., after the LiDAR scan) workflow processes (e.g., accurate light scout measurement, proper patient positioning and automated landmarking, etc.) and post-processing steps (e.g., image reconstruction). The disclosed embodiments provide a holistic framework for including a LiDAR scanning system in a CT system to improve overall efficiency and robustness of the workflow processes and post-processing steps.

Figure 2:
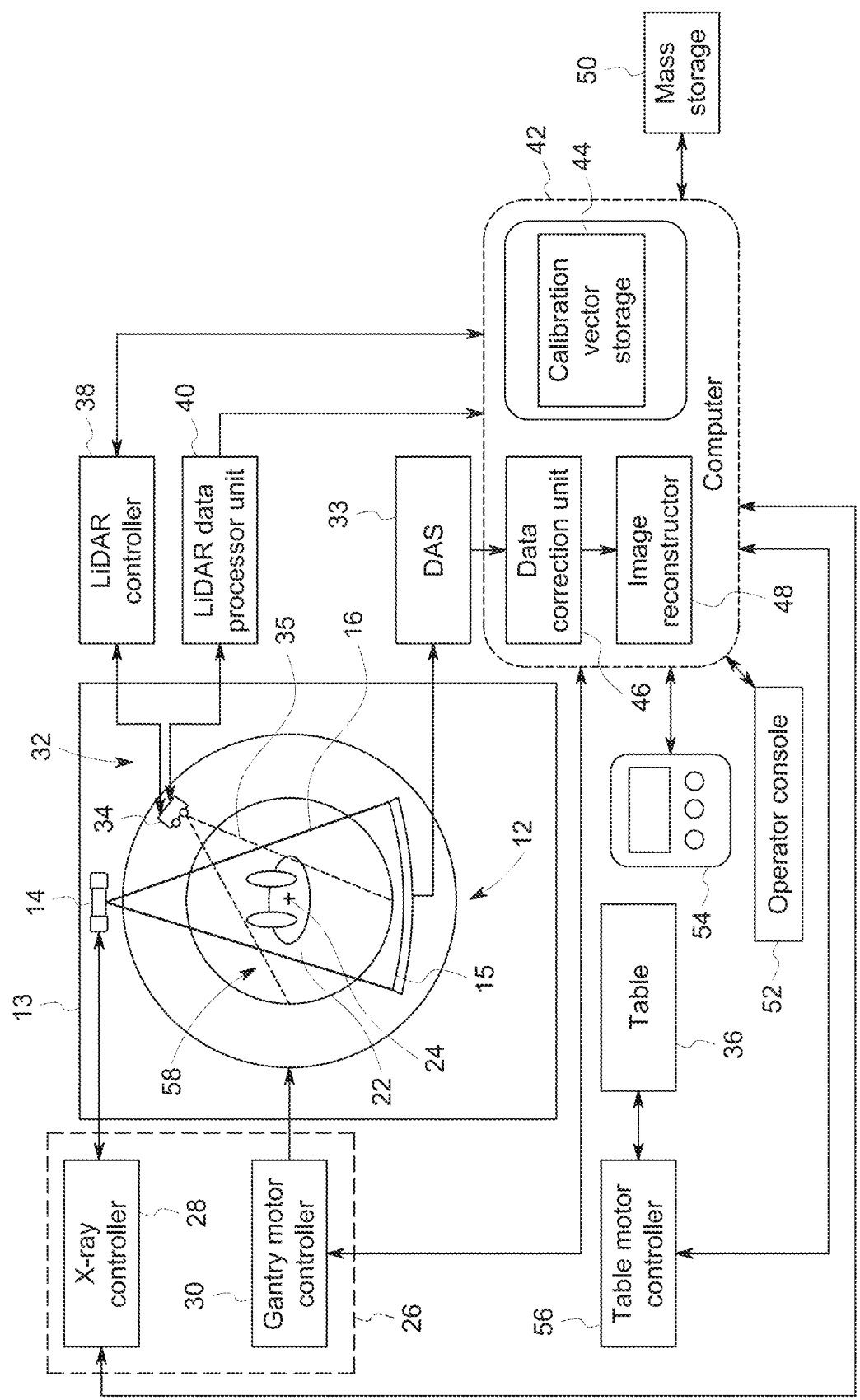
FIG. 2 is a block diagram of the CT imaging system in FIG. 1, in accordance with aspects of the present disclosure.

With the preceding in mind and referring to FIGS. 1 and 2, a CT imaging system 10 is shown, by way of example. The CT imaging system 10 includes a gantry 12 coupled having a housing 13 (e.g., gantry housing). The gantry 12 has a rotating component and a stationary component. The gantry 12 has an X-ray source 14 that projects a beam of X-rays 16 toward an X-ray detector assembly or X-ray detector array 15 (e.g., having a plurality of detector modules) on the opposite side of the gantry 12. The X-ray source 14 and the X-ray detector assembly 15 are disposed on the rotating portion of the gantry 12. The X-ray detector assembly 15 is coupled to data acquisition systems (DAS) 33. The plurality of detector modules of the X-ray detector assembly 15 detect the projected X-rays that pass through a patient or subject 22, and DAS 33 converts the data to digital signals for subsequent processing. Each detector module of the X-ray detector assembly 15 in a conventional system produces an analog electrical signal that represents the intensity of an incident X-ray beam and hence the attenuated beam as it passes through the patient 22. During a scan to acquire X-ray projection data, gantry 12 and the components mounted thereon rotate about a center of rotation 24 (e.g., isocenter) so as to collect attenuation data from a multitude of view angles relative to the imaged volume.

Rotation of gantry 12 and the operation of X-ray source 14 are governed by a control mechanism 26 of CT system 10. Control mechanism 26 includes an X-ray controller 28 that provides power and timing signals to the X-ray source 14 and a gantry motor controller 30 that controls the rotational speed and position of gantry 12.

The imaging system 10 also includes a light detection and ranging (LiDAR) scanning system 32 physically coupled to the imaging system 10. The LiDAR scanning system 32 includes one or more LiDAR scanners or instruments 34. As depicted, the LiDAR scanning system 32 has one LiDAR scanner 34. The one or more LiDAR scanners 34 are utilized to acquire depth dependent information (LiDAR data or light images) of the patient 22 with high spatial fidelity. The depth dependent information is utilized in subsequent workflow processes for a CT scan. The one or more LiDAR scanners 34 emit pulsed light 35 (e.g., laser) at the patient 22 and detect the reflected pulsed light from the patient 22. The LiDAR scanning system 32 is configured to acquire the LiDAR data from multiple different views (e.g., at different angular positions relative to the axis of rotation 24).

In certain embodiments, as depicted in FIGS. 1 and 2, the LiDAR scanner 34 is coupled to the gantry 12. In particular, the LiDAR scanner 34 is disposed within the gantry housing 13 outside a scan window. The LiDAR scanner 34 is rotated across the patient 22 to acquire the LiDAR data at the different angular positions. In certain embodiments, multiple LiDAR scanners 34 may be coupled to the gantry 12 and rotated to acquire the LiDAR data at the different angular positions.

In certain embodiments, multiple LiDAR scanners 34 may be coupled to the gantry 12 in fixed positions but disposed at different angular positions (e.g., relative to axis of rotation 24). The LiDAR scanners 34 in fixed positions may acquire the LiDAR data at the same time while remaining stationary.

In certain embodiments, the LiDAR scanning system 32 may be external to the gantry 12 but still physically coupled to the imaging system 10. For example, multiple LiDAR scanners 34 may be coupled to a LiDAR panel (e.g., at different angular positions relative to the axis of rotation 24) that is coupled to a guide rail system. The guide rail system may be coupled to the gantry housing 13 or a table 36 of the system 10. The guide rail system may be configured to move the LiDAR panel toward and away from the gantry 12. In certain embodiments, the guide rail system may also be configured to rotate the LiDAR panel about the axis of rotation 24.

The LiDAR scanning system 32 includes a LiDAR controller 38 configured to provide timing and control signals to the one or more LiDAR scanners 34 for acquiring the LiDAR data at the different angular positions. The LiDAR data may be acquired prior to, during, and/or subsequent to a CT scan of the patient 22. The LiDAR scanning system 32 also includes a LiDAR data processing unit 40 that receives or obtains the LiDAR data from the one or more LiDAR scanners 34. The LiDAR data processing unit 40 utilizes time of flight information of the reflected pulsed light and processes the LiDAR data (e.g., acquired at the different views) to generate an accurate 3D measurement of the patient 22. The 3D measurement of the patient 22 has a high spatial resolution (e.g., sub mm accuracy). As noted above, the 3D measurement may be utilized in subsequent workflow processes of a CT scan. For example, the 3D measurement may be utilized as an accurate light scout measurement (e.g., for modifying scan acquisition parameters). The 3D measurement may also be utilized for proper patient positioning (e.g., for modifying or optimizing patient position parameters) and automated landmarking. The 3D measurement may further be utilized for post-processing such as image reconstruction of the CT scan data (e.g., modifying reconstruction parameters).

The 3D measurement information from the LiDAR scanning system 32 (e.g., from the LiDAR data processing unit 40) and the scan data from the DAS 33 is input to a computer 42. The computer 42 includes a calibration vector storage 44 (e.g., for storing calibration parameters and calibration protocols for acquiring the CT scan data). The 3D measurement information obtained from the LiDAR scanning system 32 may be utilized in determining the calibration parameters utilized. The computer 42 also includes a data correction unit 46 for processing or correcting the CT scan data from the DAS 33. The computer 42 further includes an image reconstructor 48. The image reconstructor 48 receives sampled and digitized X-ray data from DAS 33 and performs high-speed reconstruction. The reconstructed image is applied as an input to the computer 42, which stores the image in a mass storage device 50. Computer 42 also receives commands and scanning parameters from an operator via console 52. An associated display 54 allows the operator to observe the reconstructed image as well as the 3D measurement data and other data from the computer 42. The operator supplied commands and parameters are used by computer 42 to provide control signals and information to the DAS 33, X-ray controller 28, gantry motor controller 30, and the LiDAR controller 38. In addition, computer 42 operates a table motor controller 56, which controls a motorized table 36 to position the patient 22 relative to the gantry 12. Particularly, table 36 moves portions of the patient 22 through a gantry opening or bore 58.

The computer 42 and the LiDAR processor unit 40 include may each include processing circuitry. The processing circuitry may be one or more general or application-specific microprocessors. The processing circuitry may be configured to execute instructions stored in a memory to perform various actions. For example, the processing circuitry may be utilized for receiving or obtaining LiDAR data acquired with the LiDAR scanning system 32. In addition, the processing circuitry may also generate a 3D measurement of the patient 22. Further, the processing circuitry may utilize the 3D measurement in a subsequent workflow process for a CT scan of the patient with the CT imaging system 32.

Figure 3:
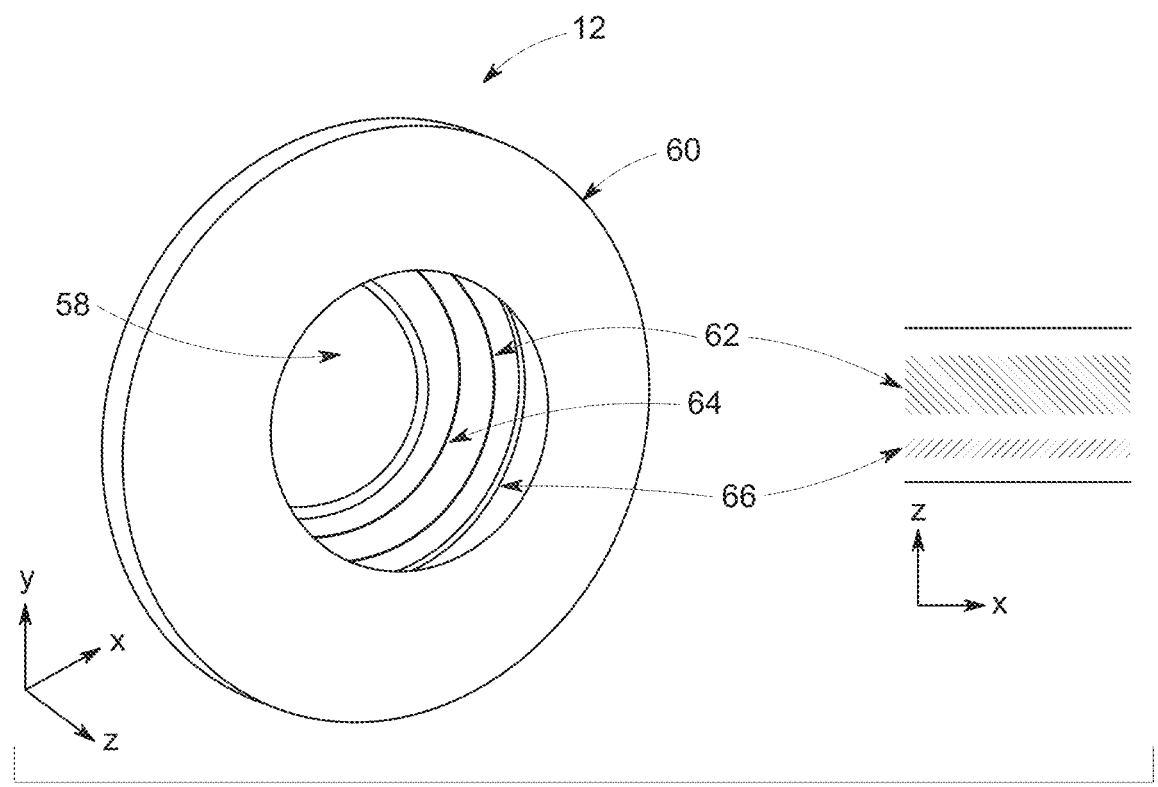
FIG. 3 is a schematic diagram of LiDAR window placement within a gantry of a CT imaging system, in accordance with aspects of the present disclosure.

FIG. 3 is a schematic diagram of LiDAR window placement within the gantry 12 of a CT imaging system. The gantry 12 includes a gantry cover 60 configured to be located on a front portion of the gantry housing adjacent the CT table. The CT imaging system includes an annular scan window 62 disposed within an interior wall 64 of the gantry 12 formed within the opening or the bore 58 of the gantry 12. The scan window 62 is made of an X-ray transparent material that enables X-rays emitted from an X-ray source to pass through an object or subject being imaged for detection by a detector. The scan window 62 is constructed so as to be fitted between components of the housing of the gantry 12 (e.g., front and back covers) to fill a gap. During an imaging session, a subject or patient is moved within the bore 58. The scan window 62 self-supports and acts as a safety barrier to keep the subject or patient from contacting rotating components within the gantry 12.

As depicted, an annular LiDAR window 66 is also disposed within the interior wall 64 of the gantry 12 formed within the bore 58 of the gantry 12. The LiDAR window 66 is made of a material transparent to the pulsed light (e.g., laser) emitted by one or more LiDAR scanners disposed within gantry 12 toward the object or subject and reflected back to the one or more LiDAR scanners. The LiDAR window 66 is disposed between scan window 62 and the gantry cover 60 in the Z-direction. In particular, the LiDAR window 66 is disposed between the scan window 62 and a front of the gantry 12 adjacent the CT table. During an imaging session, a subject or patient is moved within the bore 58. The LiDAR window 66 also self-supports and acts as a safety barrier to keep the subject or patient from contacting components (e.g., sometimes rotating components) within the gantry 12. The one or more LiDAR scanners may be located within the gantry 12 behind the LiDAR window 66. In certain embodiments, the one or more LiDAR scanners 34 are stationary during acquisition of LiDAR data. In certain embodiments, the one or more LiDAR scanners rotate during acquisition of LiDAR data. The LiDAR window 66 is located outside the region of the subject or object being scanned by the CT system.

Figure 4:
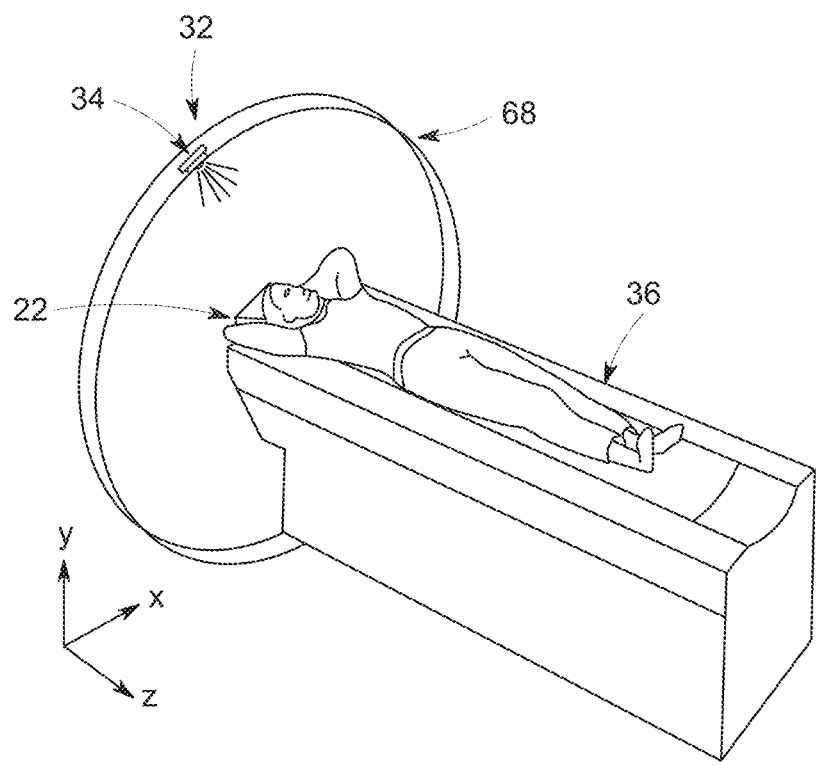
FIG. 4 is a perspective view of a schematic diagram of a LiDAR scanning system relative to a patient on a CT table, in accordance with aspects of the present disclosure.

FIG. 4 is a perspective view of a schematic diagram of the LiDAR scanning system 32 relative to the patient on the CT table 36. With the exception of the LiDAR scanning system 32, the components of the gantry are not shown for simplification. The LiDAR scanning system 32 includes an annular panel 68 (e.g., LiDAR panel). One or more LiDAR scanners 34 may be coupled to the LiDAR panel 68. As depicted, a single LiDAR scanner 34 is coupled to the LiDAR panel 68. In certain embodiments, multiple LiDAR scanners 34 may be disposed at different circumferential positions (e.g., different angular positions relative to the axis of rotation 24 in FIG. 2) along the LiDAR panel 68. The LiDAR panel 68 is disposed within the inner wall of the gantry formed within the bore of the gantry. In particular, the LiDAR panel 68 and associated one or more LiDAR scanners 34 are located beneath the LiDAR window 66 in FIG. 3. The LiDAR panel 68 and associated LiDAR scanners 34 are arranged in a concentric manner with the LiDAR window 66 (e.g., relative to the axis of rotation 24) with the LiDAR window 66 being located radially closer (in the Y-direction) than the LiDAR panel 68 and associated LiDAR scanners 34 to the axis of rotation 24. In certain embodiments, the LiDAR panel 68 and associated LiDAR scanners 34 remain in a fixed position, while LiDAR scanners 34 acquire the LiDAR data at different angular positions. In certain embodiments, the LiDAR panel 68 and one or more associated LiDAR scanners 34 rotate to acquire the LiDAR data.

Figure 5A:
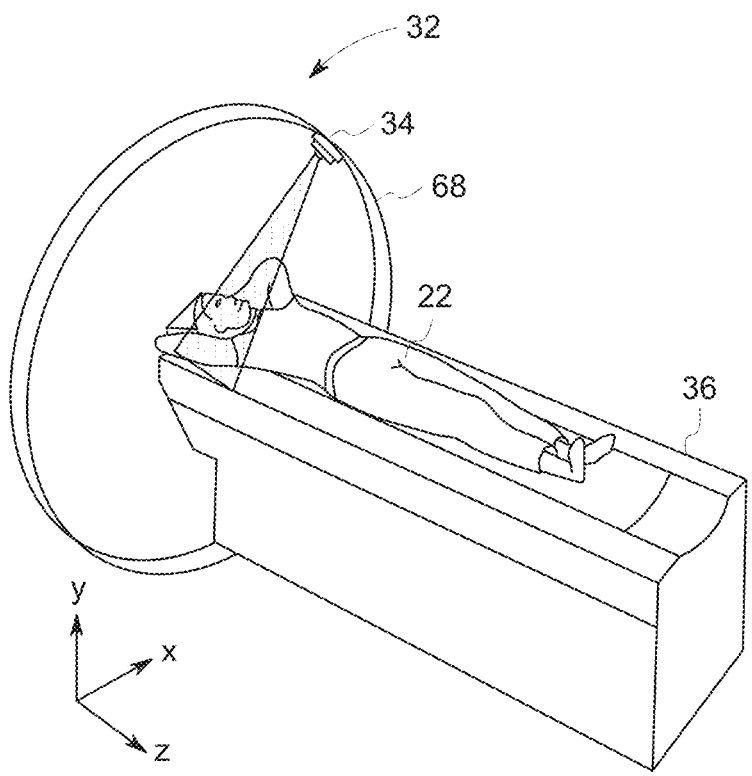
FIGS. 5A-5C depict a single LiDAR scanner obtaining data at different angular positions, in accordance with aspects of the present disclosure.
Figure 5B:
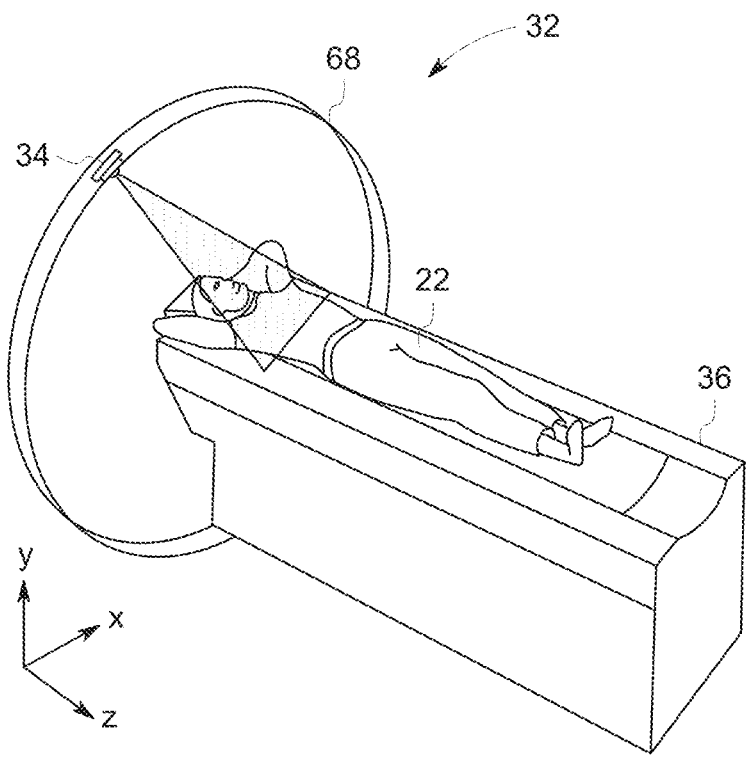
Figure 5C:
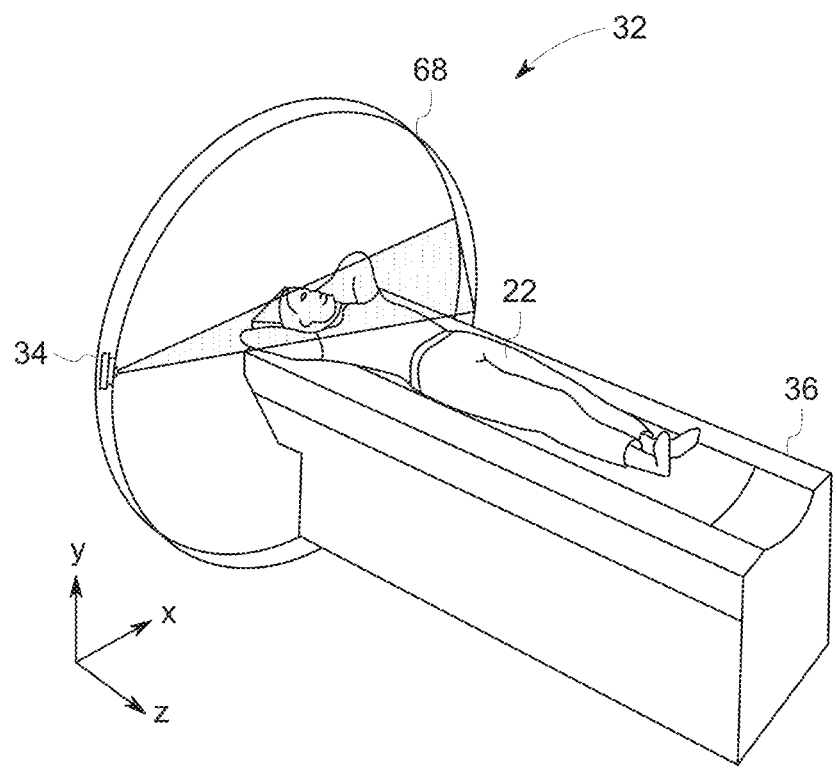
Figure 6:
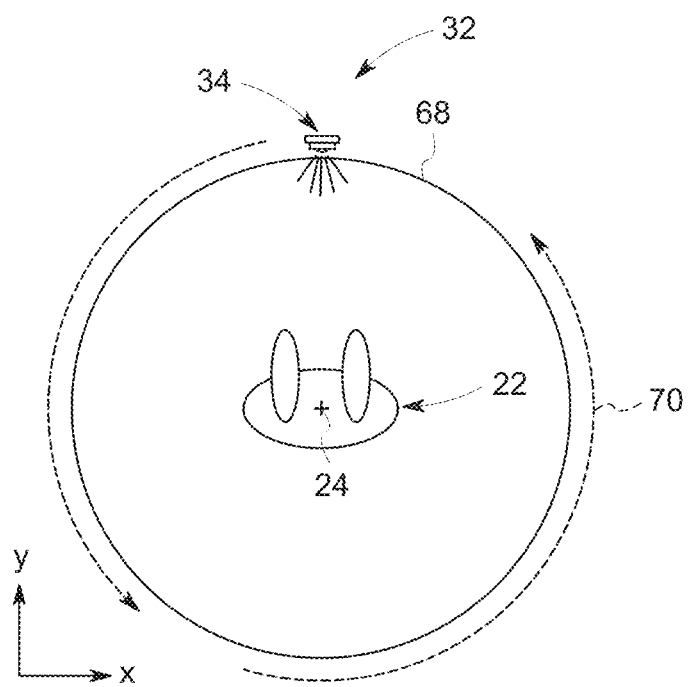
FIG. 6 is a pictorial representation of a single LiDAR scanner rotating 360 degrees across a patient for data acquisition, in accordance with aspects of the present disclosure.

FIGS. 5A-5C depict a single LiDAR scanner 34 obtaining data at different angular positions. With the exception of the LiDAR scanning system 32, the components of the gantry are not shown for simplification. As depicted in FIGS. 5A-5C, the single LiDAR scanner 34 is coupled to the LiDAR panel 68. The LiDAR scanner 34 rotates (e.g., about the axis of rotation 24 in FIG. 2) to acquire the LiDAR data. In particular, the LiDAR scanner 34 (and LiDAR panel 68) rotates to different angular positions to acquire different views of LiDAR data. The data acquired at the different angular positions can then be combined later to generate the 3D measurement of the patient 22. It should be noted although the patient 22 is depicted outside an area of the gantry where the LiDAR panel 68 is located, in certain embodiments, the patient 22 may be moved into the gantry via the table 36 so that the LiDAR panel 68 is disposed about a portion of the patient 22. As depicted in FIG. 6, the single LiDAR scanner 34 may rotate up to 360 degrees in a circumferential direction 70 (e.g., relative to the axis of rotation 24) across the target (i.e., the patient 22) to acquire the LiDAR data at the different angular positions.

Figure 7:
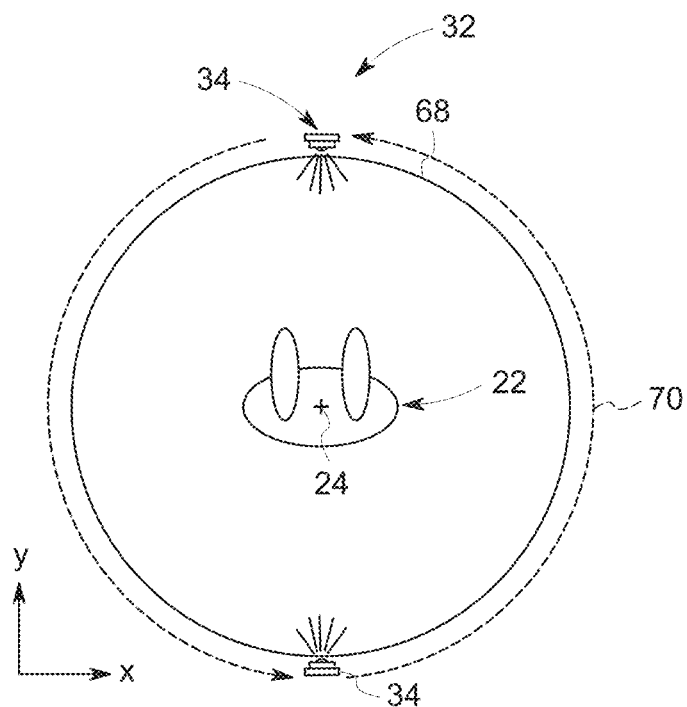
FIG. 7 is a pictorial representation of multiple LiDAR scanners rotating across a patient for data acquisition, in accordance with aspects of the present disclosure.

In certain embodiments, as depicted in FIG. 7, multiple LiDAR scanners 34 may be coupled to the LiDAR panel 68. As depicted, two LiDAR scanners 34 are coupled to the LiDAR panel 68. The number of LiDAR scanners 34 coupled to the LiDAR panel 68 may vary (e.g., 2, 3, 4, 5, 6, or other number of LiDAR scanners 34). The LiDAR scanners 34 are circumferentially 70 spaced apart from each other along the LiDAR panel 68. Each LiDAR scanner 34 (and the LiDAR panel 68) rotates about the axis of rotation 24. In certain embodiments, each LiDAR scanner 34 rotates only a portion of the 360 degrees across the patient 22 to acquire the LiDAR data. For example, as depicted in FIG. 7, each LiDAR scanner 34 may rotate only up to approximately 180 degrees circumferentially 70. Thus, together both the LiDAR scanners 34 may cover 360 degrees about the patient 22. In certain embodiments, with three LiDAR scanners 34 coupled to the LiDAR panel 68, each LiDAR scanner 34 may cover up to approximately 120 degrees circumferentially 70. In certain embodiments, with four LiDAR scanners 34 coupled to the LiDAR panel 68, each LiDAR scanner 34 may cover up to approximately 90 degrees circumferentially 70. Thus, no matter the number of LiDAR scanners 34 coupled to the LiDAR panel 68, each LiDAR scanner 34 may cover an equal portion of the 360 degrees about the patient 22. In certain embodiments, when multiple LiDAR scanners 34 are coupled to the LiDAR panel 68, one or more of the LiDAR scanners 34 cover a different angular range about the patient 22 relative to the other LiDAR scanners 34. For example, in the case of two LiDAR scanners 34, one LiDAR scanner 34 may cover 120 degrees and the other LiDAR scanner may cover 240 degrees. In certain embodiments, when multiple LiDAR scanners 34 are coupled to the LiDAR panel 68, each LiDAR scanner 34 may cover up to 360 degrees to provide redundancy in the acquired data. In certain embodiments, the LiDAR scanning system 32 may not cover 360 degrees about the patient 22 when certain angular positions are obstructed (e.g., by a bottom of the CT table).

Figure 8:
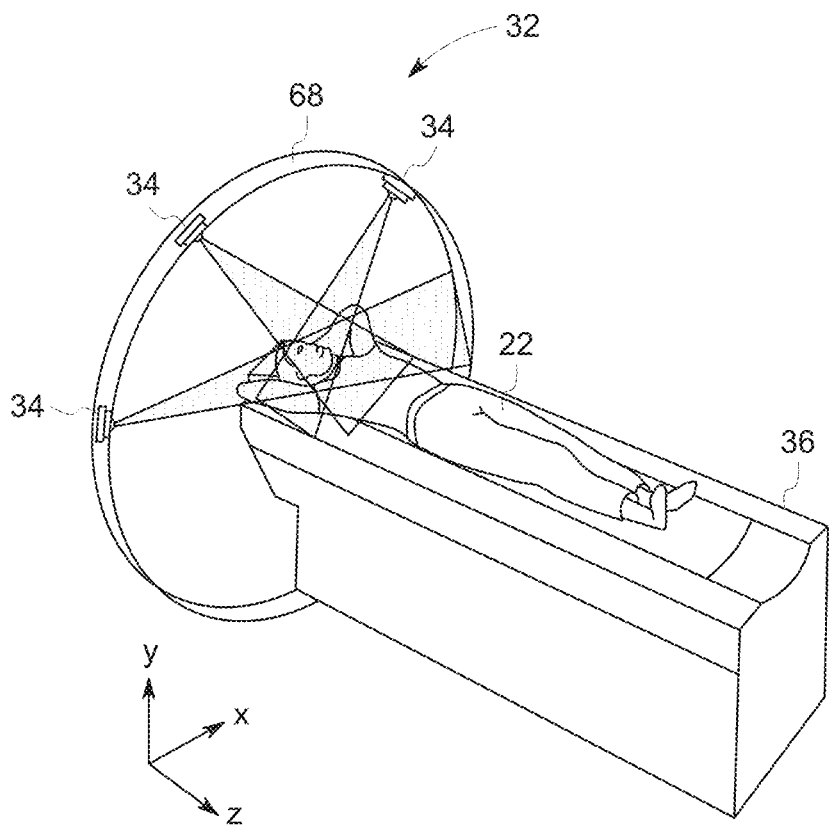
FIG. 8 is a perspective view of a schematic diagram of multiple LiDAR scanners obtaining data of a patient at different angular positions at the same time; in accordance with aspects of the present disclosure.
Figure 9:
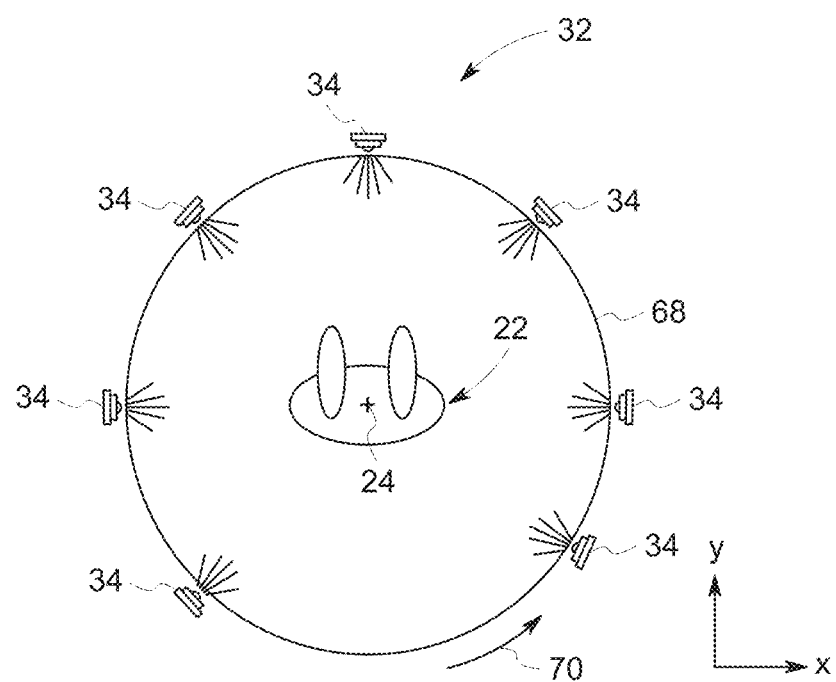
FIG. 9 is a pictorial representation of multiple LiDAR scanners placed 360 degrees across the patient for data acquisition, in accordance with aspects of the present disclosure.

FIGS. 8 and 9 illustrate utilizing multiple LiDAR scanners 34 to obtain data of the patient 22 at different angular positions at the same time. With the exception of the LiDAR scanning system 32, the components of the gantry are not shown for simplification. As depicted, the LiDAR scanning system 32 includes multiple LiDAR scanners 34 coupled to the LiDAR panel 68. The LiDAR scanners 34 are circumferentially 70 spaced apart (e.g., relative to the axis of rotation 24) from each other along the LiDAR panel 68. The LiDAR scanners 34 are disposed in fixed positions (e.g., different angular positions) along the LiDAR panel 68. Both the LiDAR scanners 34 and LiDAR panel 68 remain stationary during acquisition of the LiDAR data. In particular, LiDAR data is acquired by each of the LiDAR scanners 34 scanners at the same time, thus, providing LiDAR data at different views (i.e., different angular positions). The data acquired at the different angular positions can then be combined later to generate the 3D measurement of the patient 22.

Figure 10:
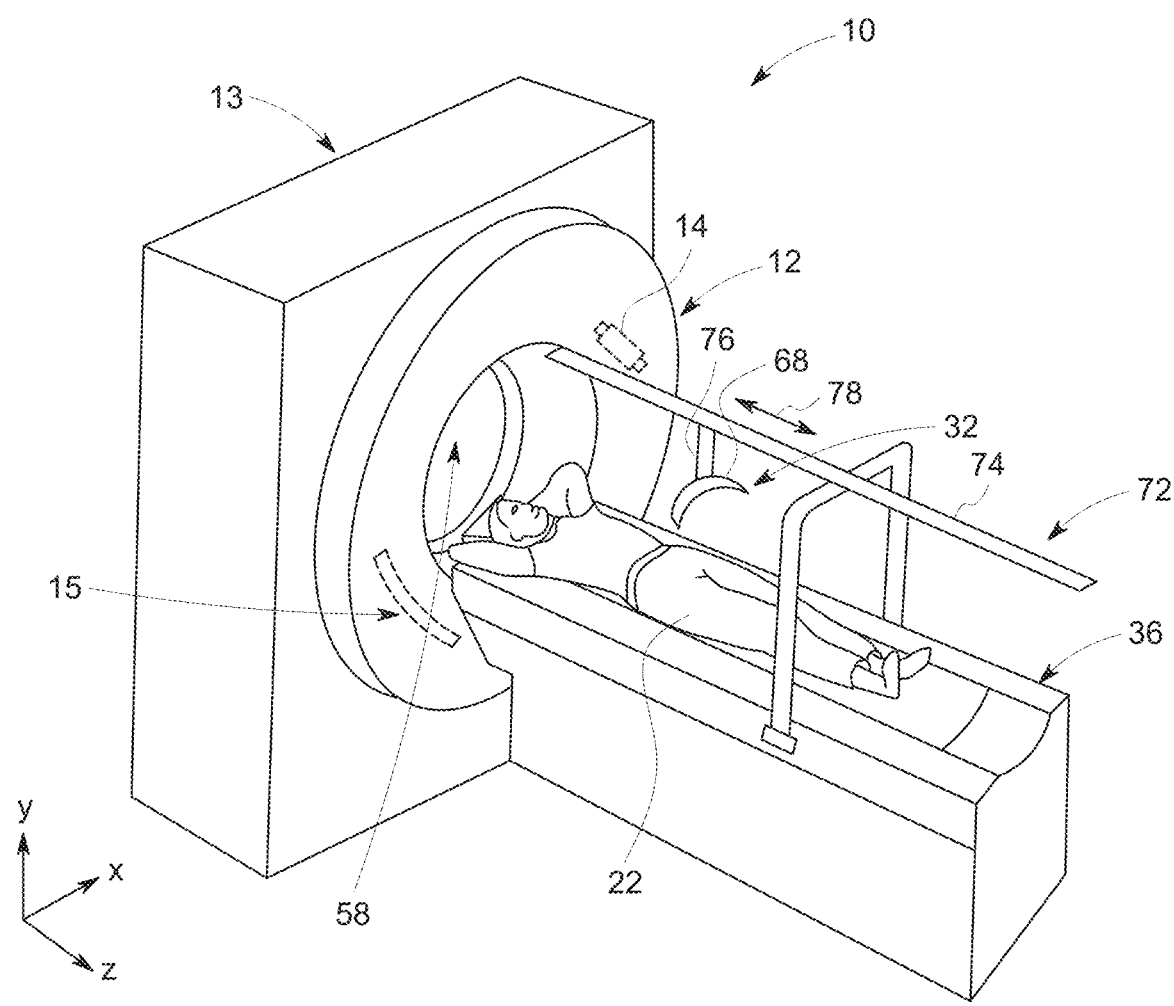
FIG. 10 is a pictorial representation of an external LiDAR scanning system coupled to a CT table, in accordance with aspects of the present disclosure.

In certain embodiments, the LiDAR scanning system 32 may be external to the gantry 12 but still physically coupled to the imaging system 10. FIG. 10 is a pictorial representation of an external LiDAR scanning system 32 coupled to the CT table 36. The LiDAR scanning system 32 is coupled to a guide rail system 72. The guide rail system 72 is coupled to the table 36. The guide rail system 72 is configured to move the LiDAR scanning system 32 toward and away from the gantry 12 (e.g., in the Z-direction along the longitudinal length of the patient 22). The guide rail system 72 includes a main guide rail 74 coupled to a support structure 76 that supports the main guide rail 74. The main guide rail 74 extends in the Z-direction above the table 36 (e.g., along a longitudinal length of the table 36). The support structure 76 is coupled to the table 36. The support structure 76 extends in a vertical direction (e.g., in the Y-direction) from the table 36 and then extends in a horizontal direction (e.g., in the X-direction) to couple to the main guide rail 74. The configuration of the support structure 76 and how it is coupled to both the table 36 and the main guide rail 74 may vary.

The LiDAR scanning system 32 includes the LiDAR panel 68 (e.g., having an arc shape). The LiDAR panel 68 includes a plurality of LiDAR scanners (see FIG. 13) coupled to it. The plurality LiDAR scanners are circumferentially spaced apart along the arc of the LiDAR panel 68 at different angular positions to enable the acquisition of different views of LiDAR data. The LiDAR panel 68 is coupled to the guide rail system 72. In particular, the LiDAR panel 68 is coupled to the main guide rail 74 via a vertical support stanchion 76 (e.g., post or bar). The guide rail system 72 is configured to move the LiDAR panel 68 (and the vertical support stanchion) back and forth toward the gantry 12 as indicated by arrow 78 (in the Z-direction) along the main guide rail 74. The main guide rail 74 may include an actuation system (e.g., chain actuator, electro-mechanical linear actuator, or any other mechanism for facilitating linear movement along the main guide rail 74). In certain embodiments, the guide rail system 72 is configured to circumferentially move the LiDAR panel 68 along its arc. In particular, the guide rail system 72 may enable the LiDAR panel 68 to rotate circumferentially (e.g., relative to the axis of rotation 24 in FIG. 2) so that the LiDAR panel 68 is moving with respect to the vertical support stanchion 76. The LiDAR panel 68 may rotate both clockwise and counterclockwise (e.g., relative to the axis of rotation 24 in FIG. 2). Rotational movement of the LiDAR panel 68 enables the acquisition of LiDAR data from additional different angular positions.

Figure 11:
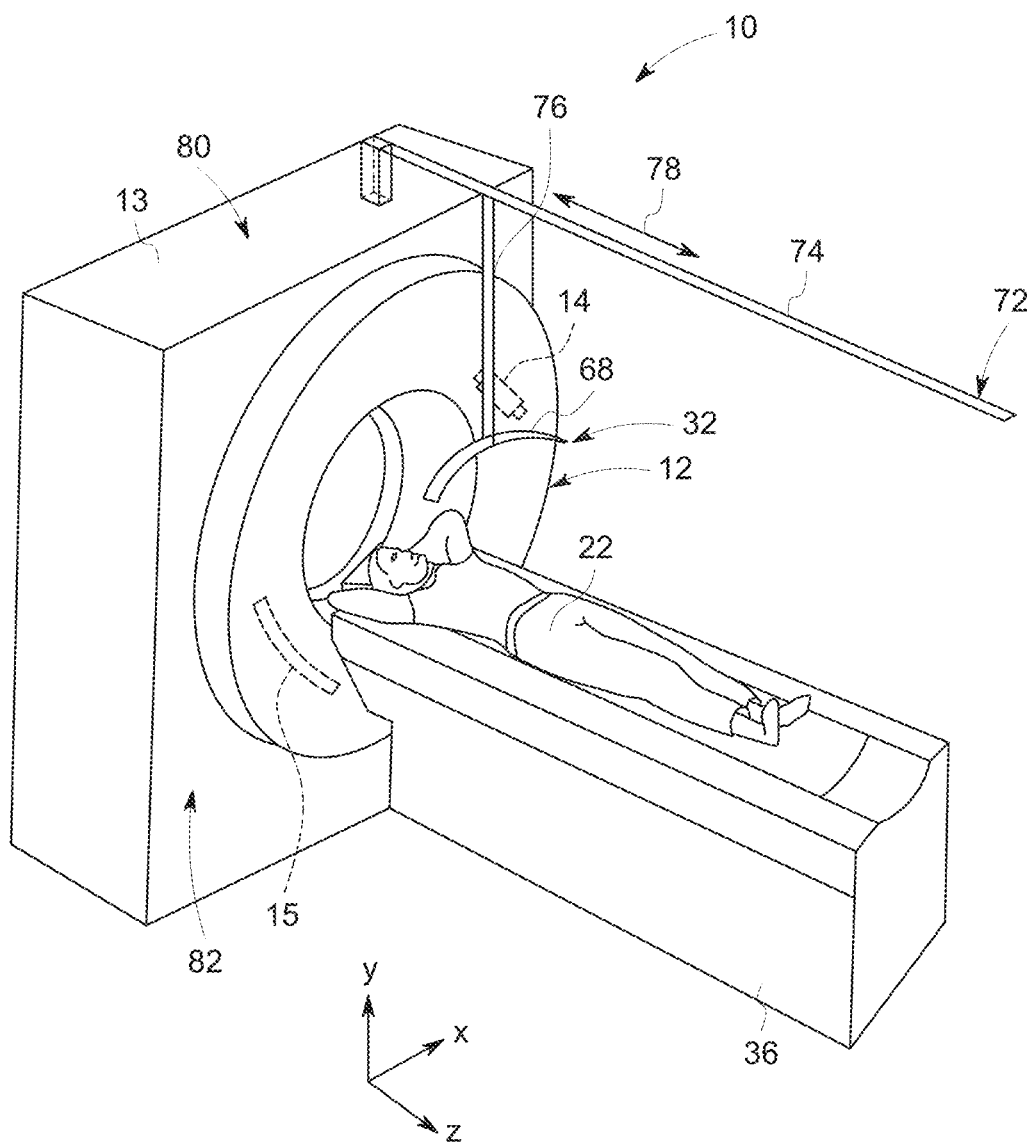
FIG. 11 is a pictorial representation of an external LiDAR scanning system coupled to a gantry housing of a CT imaging system, in accordance with aspects of the present disclosure.

FIG. 11 is a pictorial representation of the external LiDAR scanning system 32 coupled to the gantry housing 13 of the CT imaging system 10. The LiDAR scanning system 32 is coupled to the guide rail system 72. The guide rail system 72 is coupled to the gantry housing 13. The guide rail system 72 is configured to move the LiDAR scanning system 32 toward and away from the gantry 12 (e.g., in the Z-direction along the longitudinal length of the patient 22). The guide rail system 72 includes the main guide rail 74 directly coupled to a top portion 80 of the gantry housing 13. In certain embodiments, the main guide rail 74 may be coupled to a different portion (e.g., front portion 82) of the gantry housing 13. The main guide rail 74 extends in the Z-direction above the table 36 (e.g., along a longitudinal length of the table 36). How the main guide rail 74 is coupled to the gantry housing 13 may vary.

The LiDAR scanning system 32 includes the LiDAR panel 68 (e.g., having an arc shape). The LiDAR panel 68 includes a plurality of LiDAR scanners (see FIG. 13) coupled to it. The plurality LiDAR scanners are circumferentially spaced apart along the arc of the LiDAR panel 68 at different angular positions to enable the acquisition of different views of LiDAR data. The LiDAR panel 68 is coupled to the guide rail system 72. In particular, the LiDAR panel 68 is coupled to the main guide rail 74 via the vertical support stanchion 76 (e.g., post or bar). The guide rail system 72 is configured to move the LiDAR panel 68 (and the vertical support stanchion) back and forth toward the gantry 12 as indicated by arrow 78 (in the Z-direction) along the main guide rail 74. The main guide rail 74 may include an actuation system (e.g., chain actuator, electro-mechanical linear actuator, or any other means for facilitating linear movement along the main guide rail 74). In certain embodiments, the guide rail system 72 is configured to circumferentially move the LiDAR panel 68 along its arc. In particular, the guide rail system 72 may enable the LiDAR panel 68 to rotate circumferentially (e.g., relative to the axis of rotation 24 in FIG. 2) so that the LiDAR panel 68 is moving with respect to the vertical support stanchion 76. The LiDAR panel 68 may rotate both clockwise and counterclockwise (e.g., relative to the axis of rotation 24 in FIG. 2). Rotational movement of the LiDAR panel 68 enables the acquisition of LiDAR data from additional different angular positions.

Figure 12:
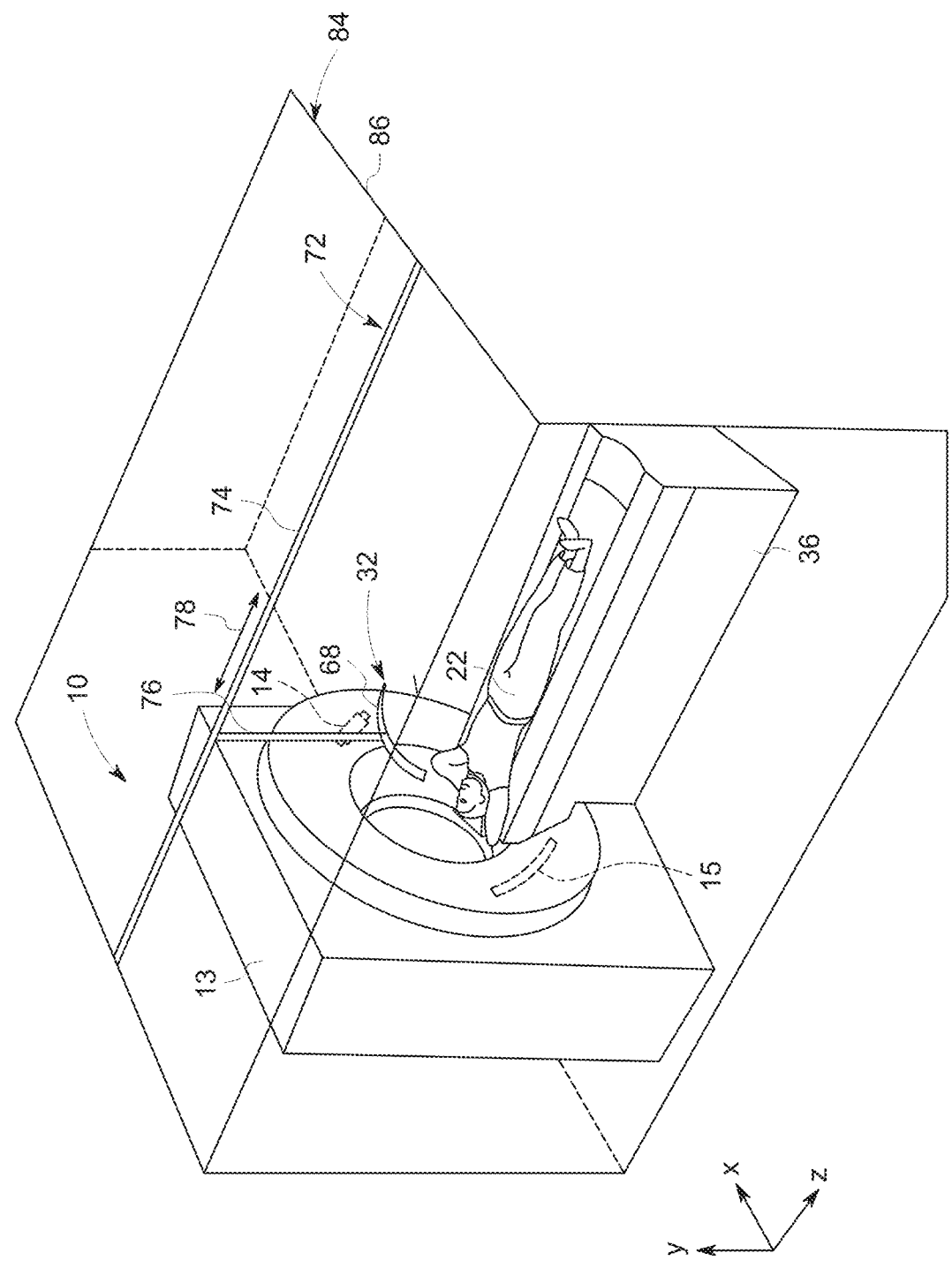
FIG. 12 is a pictorial representation of an external LiDAR scanning system coupled to a wall (e.g., ceiling) of a room housing a CT imaging system, in accordance with aspects of the present disclosure.

In certain embodiments, the LiDAR scanning system 32 may be external to the CT imaging system 10 but not be physically coupled to the CT imaging system 10. FIG. 12 is a pictorial representation of the external LiDAR scanning system 32 coupled to a wall of a room housing the CT imaging system 10. As depicted, the LiDAR scanning system 32 and the CT imaging system 10 are disposed within a room 84 (e.g., imaging room). The LiDAR scanning system 32 is coupled to the guide rail system 72. The guide rail system 72 is coupled to a wall 86 (e.g., ceiling) of the room 84. The guide rail system 72 is configured to move the LiDAR scanning system 32 toward and away from the gantry 12 (e.g., in the Z-direction along the longitudinal length of the patient 22). The guide rail system 72 includes the main guide rail 74 directly coupled to or mounted to the wall 86. The main guide rail 74 extends in the Z-direction above the table 36 (e.g., along a longitudinal length of the table 36). How the main guide rail 74 is coupled to the wall 86 may vary. For example, the main guide rail 74 may be supported by one or more supports coupled to and extending down from the wall 86.

The LiDAR scanning system 32 includes the LiDAR panel 68 (e.g., having an arc shape). The LiDAR panel 68 includes a plurality of LiDAR scanners (see FIG. 13) coupled to it. The plurality LiDAR scanners are circumferentially spaced apart along the arc of the LiDAR panel 68 at different angular positions to enable the acquisition of different views of LiDAR data. The LiDAR panel 68 is coupled to the guide rail system 72. In particular, the LiDAR panel 68 is coupled to the main guide rail 74 via the vertical support stanchion 76 (e.g., post or bar). The guide rail system 72 is configured to move the LiDAR panel 68 (and the vertical support stanchion) back and forth toward the gantry 12 as indicated by arrow 78 (in the Z-direction) along the main guide rail 74. The main guide rail 74 may include an actuation system (e.g., chain actuator, electro-mechanical linear actuator, or any other means for facilitating linear movement along the main guide rail 74). In certain embodiments, the guide rail system 72 is configured to circumferentially move the LiDAR panel 68 along its arc. In particular, the guide rail system 72 may enable the LiDAR panel 68 to rotate circumferentially (e.g., relative to the axis of rotation 24 in FIG. 2) so that the LiDAR panel 68 is moving with respect to the vertical support stanchion 76. The LiDAR panel 68 may rotate both clockwise and counter-clockwise (e.g., relative to the axis of rotation 24 in FIG. 2). Rotational movement of the LiDAR panel 68 enables the acquisition of LiDAR data from additional different angular positions.

Figure 13:
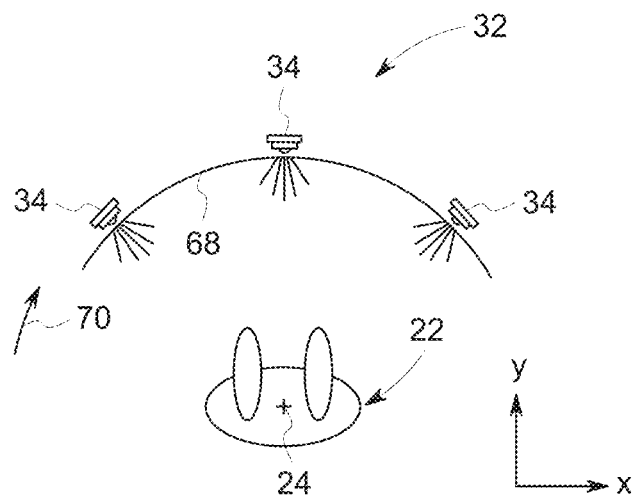
FIG. 13 is a pictorial representation of the placement of the LiDAR scanners relative to the patient for the external LiDAR scanning system of FIGS. 10-12, in accordance with aspects of the present disclosure.

FIG. 13 is a pictorial representation of the placement of the LiDAR scanners 32 relative to the patient 22 for the external LiDAR scanning system 32 of FIGS. 10-12. As depicted, the LiDAR scanning system 32 includes the LiDAR panel 68 having an arc shape that extends circumferentially 70 relative the axis of rotation 24. The LiDAR scanning system 32 includes multiple LiDAR scanners 34 coupled to the LiDAR panel 68. In particular, the LiDAR scanners 34 are circumferentially 70 spaced apart along the LiDAR panel 68 to enable the acquisition of LiDAR data at different angular positions to provide information at different views. As depicted, three LiDAR scanners 34 are coupled to the LiDAR panel 68. In certain embodiments, the number of LiDAR scanners 34 may vary. For example, the LIDAR scanning system 32 may include 2, 3, 4, 5, 6, or another number of LiDAR scanners 34 coupled to the LiDAR panel 68. In certain embodiments, a length of the LiDAR panel 68 along the arc (e.g., in the circumferential direction 70) may vary to accommodate the number of LiDAR scanners 34 coupled to the LiDAR panel 68 and/or a desired spacing between the LiDAR scanners 34 along the LiDAR panel 68.

Figure 14:
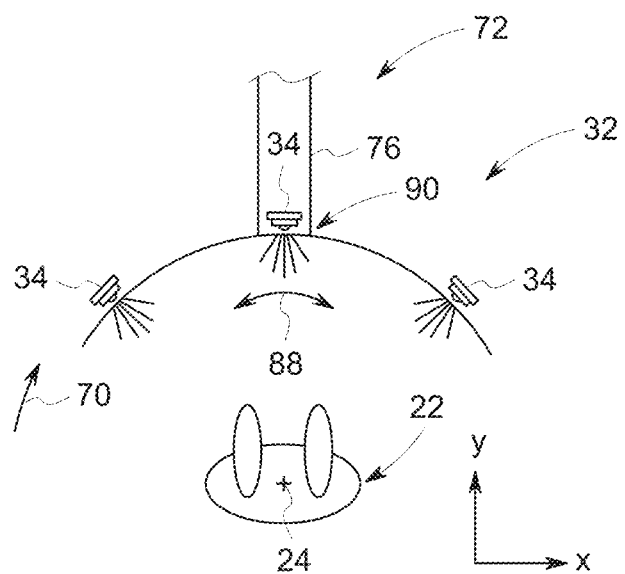
FIG. 14 is a pictorial representation of rotational movement of the external LiDAR scanning system of FIGS. 10-12 relative to the guide rail system, in accordance with aspects of the present disclosure.

As noted above, in certain embodiments, besides moving the LiDAR scanning system toward and away from the gantry, the guide rail system may also enable other types of movement of the LiDAR scanning system. FIG. 14 is a pictorial representation of rotational movement of the external LiDAR scanning system 32 of FIGS. 10-12 relative to the guide rail system 72. The external LiDAR scanning system 32 is as described in FIGS. 10-13. As depicted, the LiDAR panel 68 is coupled to the vertical support stanchion 76 of the guide rail system 72. The guide rail system 72 is configured to circumferentially 70 move the LiDAR panel 68 along its arc as indicated by arrow 88. In particular, the guide rail system 72 may enable the LiDAR panel 68 to rotate circumferentially (e.g., relative to the axis of rotation 24 in FIG. 2) so that the LiDAR panel 68 is moving with respect to the vertical support stanchion 76. In particular, the vertical support stanchion 76 maintains a vertical position as the LiDAR panel 68 moves with respect to the vertical support stanchion. The LiDAR panel 68 may rotate both clockwise and counter-clockwise relative to the axis of rotation 24. Rotational movement of the LiDAR panel 68 enables the acquisition of LiDAR data from additional different angular positions. An interface 90 between the vertical support stanchion 76 and the LiDAR panel 68 may include an actuation system (e.g., bearing-based system, electro-mechanical system, or any other mechanism for circumferentially 70 rotating the LiDAR panel 68 relative to the vertical support stanchion 76) for facilitating the rotation of the LiDAR panel 68.

Figure 15:
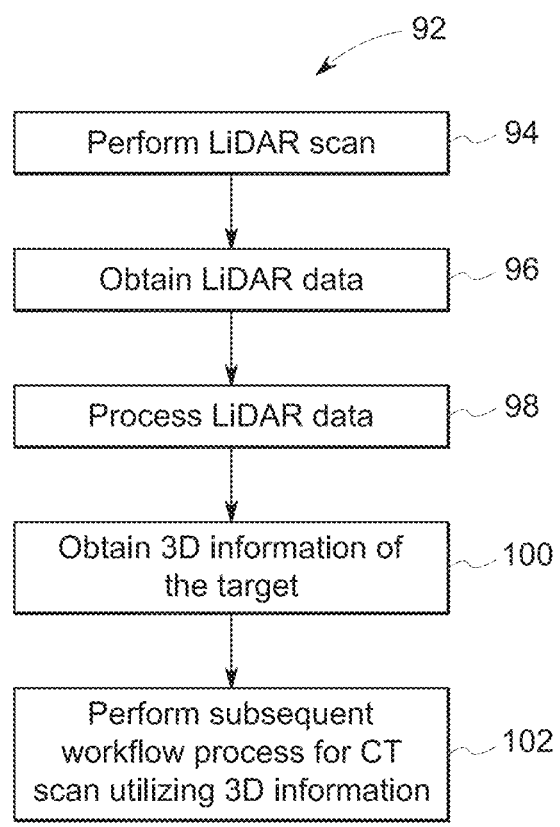
FIG. 15 is a flowchart of a method for acquiring and utilizing LiDAR data, in accordance with aspects of the present disclosure.
Figure 16C:
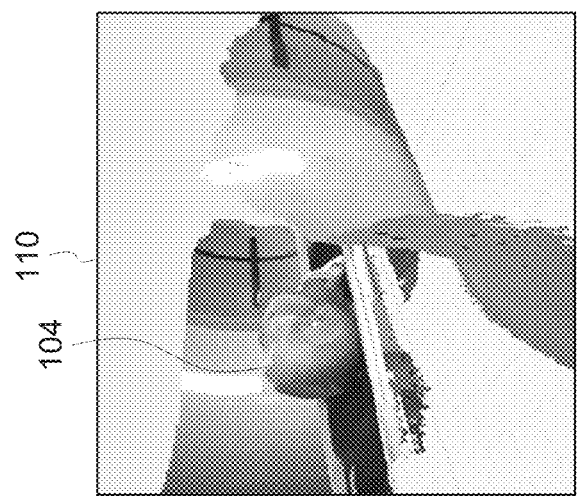
FIGS. 16A-16E are images of a LiDAR scan obtained of a head phantom.
Figure 16B:
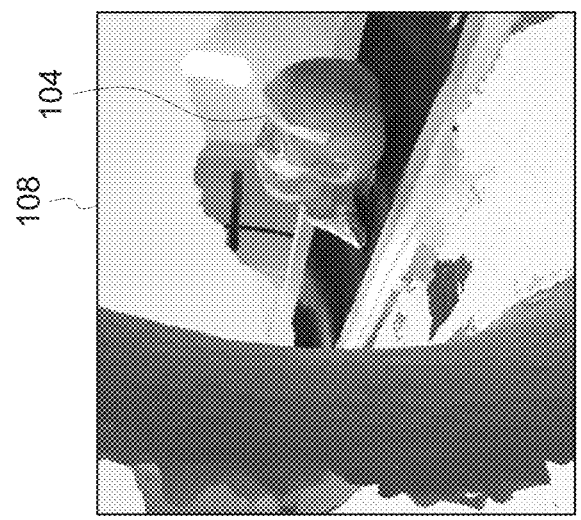
Figure 16A:
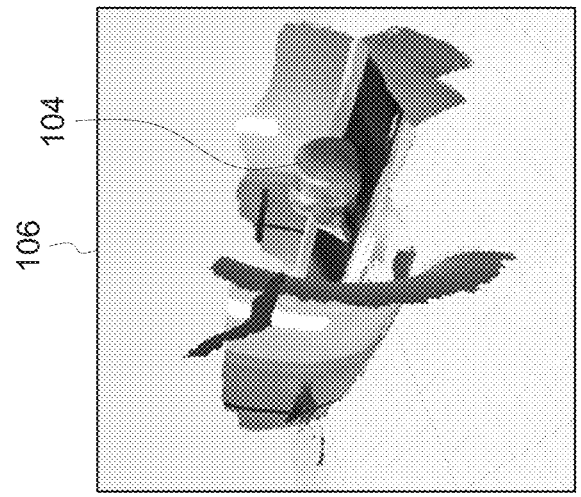
Figure 16D:
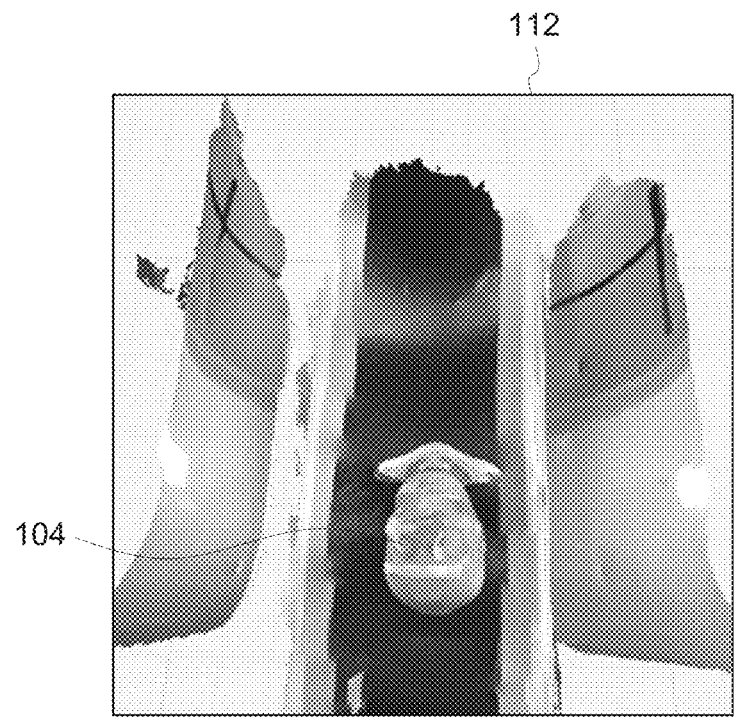
Figure 16E:
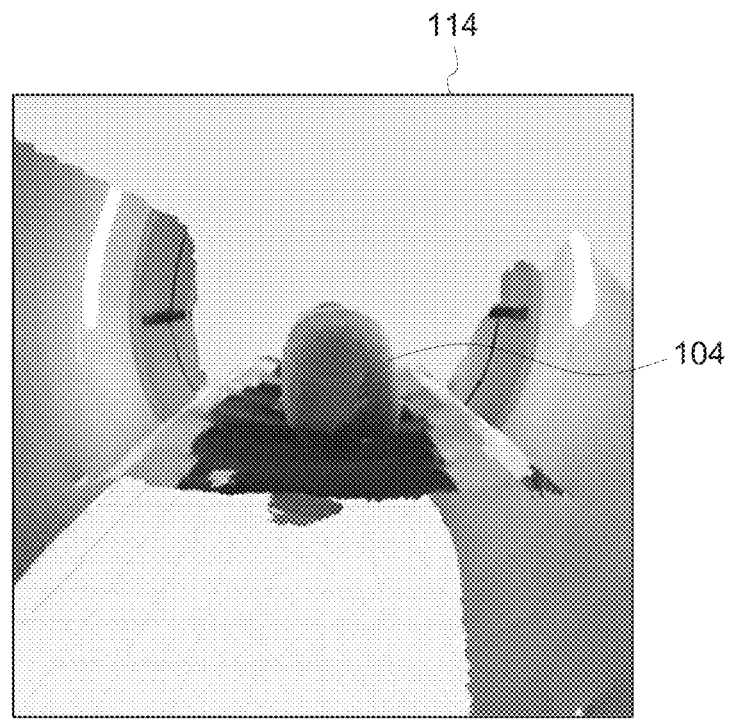

FIG. 15 is a flowchart of a method 92 for acquiring and utilizing LiDAR data. The method 92 may be performed by one or more components (e.g., processing circuitry) of the LiDAR scanning system 32 and/or the CT imaging system 10 in FIGS. 1 and 2. One or more steps of the method 92 may be performed simultaneously and/or in a different order than depicted in FIG. 15.

The method 92 includes performing a LiDAR scan (e.g., utilizing the LiDAR scanning system 32 in FIGS. 1 and 2) (block 94). The LiDAR scan is performed while the subject or target (e.g., patient) is positioned on the CT table of the CT imaging system. Depending on what subsequent workflow process of the CT scan that the LiDAR data is being utilized for, the timing of the LiDAR scan may vary relative to a CT scan of the target. In certain embodiments, the LiDAR scan may occur prior to the CT scan. In certain embodiments, the LiDAR scan may occur during the CT scan. In certain embodiments, the LiDAR scan may occur subsequent to the CT scan.

The method 92 also includes obtaining or receiving LiDAR data from the LiDAR scan (block 96). The LiDAR data represents light images of different views acquired at different angular positions (e.g., relative to axis of rotation 24 in FIG. 2). The method 92 further includes processing the LiDAR data (block 98). Processing the LiDAR includes combining the LiDAR data and generating 3D information (i.e., 3D measurement) of the target. Processing of the LiDAR data may also include changing a coordinate system, inspecting point components and values, tiling the LiDAR data, clipping points outside a defined boundary, reducing the number of points, splitting by component value, filtering the LiDAR data, and/or other processing techniques. These processing techniques may be performed prior to and/or after the generation of the 3D information. The method 92 still further includes obtaining 3D information of the target (block 100).

The method 92 yet further includes performing a subsequent workflow process for a CT scan utilizing the 3D information (i.e., the 3D measurement of the target) (block 102). The workflow processes may be pre-scan workflow processes or post-scan workflow processes. In certain embodiments, the 3D information may be utilized as a light scout measurement. For example, the 3D information may be utilized for sizing the target to determine or to modify acquisition parameters or scanning protocols. In certain embodiments, the 3D information may be utilized for proper patient positioning. For example, the 3D information may be utilized to calculate, to modify, or to optimize patient position parameters. The 3D information may also be utilized in automated landmarking. In certain embodiments, the 3D information may be utilized for capturing motion information (e.g., during the CT scan). The 3D information may be utilized to calculate or to modify reconstruction parameters for reconstructing an image of the target from the CT scan data. In certain embodiments, the parameters (e.g., scan acquisition parameters, reconstructions parameters, patient position parameters, etc.) may be calculated or modified in an iterative process. In certain embodiments, the parameters may be calculated or modified in a non-iterative process. In certain embodiments, the blocks 94-100 of the method 92 may be performed multiple times during an imaging session.

FIGS. 16A-16E are images 106, 108, 110, 112, and 114 of a LiDAR scan obtained of a head phantom 104. Images 106, 108, and 110 are different perspective views of the LiDAR scan of the head phantom 104. Images 112 and 114 are a top view and an end view, respectively, of the LiDAR scan of the head phantom 104. The images 106, 108, 110, 112, and 114 illustrate the 3D rendering of the LiDAR data generated during the LiDAR scan.

Figure 17C:
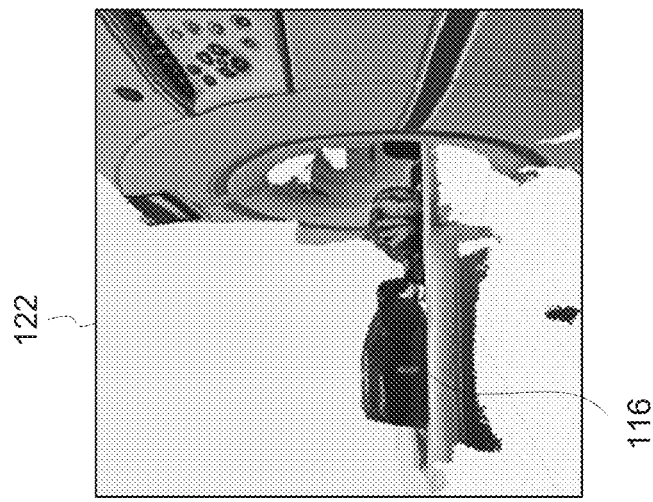
FIGS. 17A-17C are images of a LiDAR scan obtained of a chest phantom.
Figure 17B:
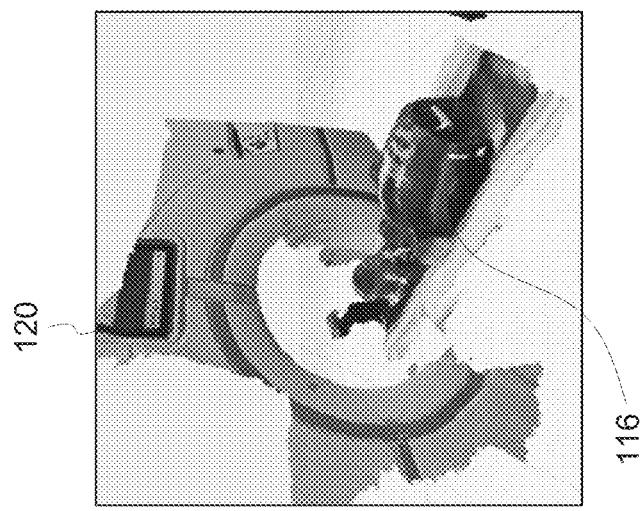
Figure 17A:
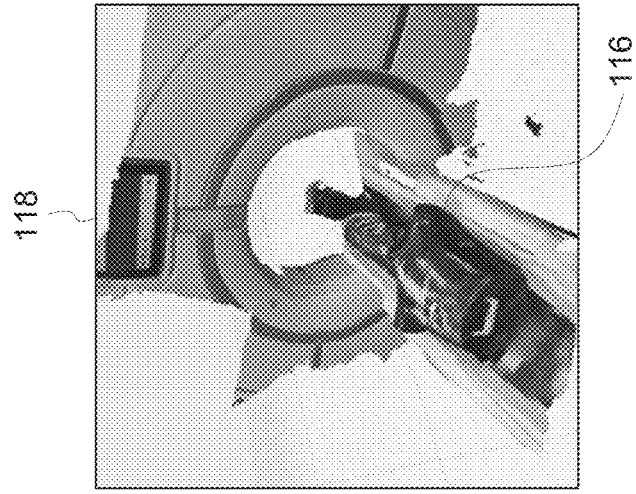

FIGS. 17A-17C are images 118, 120, and 122 of a LiDAR scan obtained of a chest phantom 116. Images 118 and 120 are different perspective views of the LiDAR scan of the chest phantom 116. Image 122 is a side view of the LiDAR scan of the chest phantom 116. The images 118, 120, and 122 illustrate the 3D rendering of the LiDAR data generated during the LiDAR scan.

Technical effects of the disclosed embodiments include providing systems and methods for generating an accurate 3D measurement of a target (e.g., patient) before or during a CT scan to be utilized in a subsequent CT workflow process for the CT scan. The present disclosure provides systems and methods for incorporating LiDAR based techniques with a CT imaging system to aid various workflows more efficiently. The disclosed embodiments provide a holistic framework for including a LiDAR scanning system in a CT system to improve overall efficiency and robustness of the workflow processes and post-processing steps.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical imaging system, comprising:
   a computed tomography (CT) imaging system, comprising:
      a gantry having a bore, rotatable about an axis of rotation;
      a table configured to move a subject to be imaged into and out of the bore of the gantry;
      a radiation source mounted on the gantry and configured to emit an X-ray beam; and
      a detector configured to detect the X-ray beam emitted by the radiation source;
   a light detection and ranging (LiDAR) scanning system physically coupled to the CT imaging system, wherein the LiDAR scanning system is configured to acquire data of the subject from different angular positions relative to the axis of rotation; and
   processing circuitry configured to receive the data acquired with the LiDAR scanning system, to generate a three-dimensional (3D) measurement of the subject, and to utilize the 3D measurement in a subsequent workflow process for a CT scan of the subject with the CT imaging system, wherein the CT imaging system comprises a gantry housing, wherein the LiDAR scanning system comprises one or more LiDAR scanners configured to acquire the data, and the one or more LiDAR scanners are disposed within the gantry housing, and wherein the gantry housing comprises both a scan window and a LiDAR window disposed about the bore, and wherein the one or more LiDAR scanners are disposed beneath the LiDAR window between the scan window and a side of the gantry housing adjacent the table.

2. The medical imaging system of claim 1, wherein the one or more LiDAR scanners are configured to rotate about the axis of rotation to acquire the data at the different angular positions.

3. The medical imaging system of claim 1, wherein the LiDAR scanning system comprises a single LiDAR scanner.

4. The medical imaging system of claim 1, wherein the LiDAR scanning system comprises a plurality of LiDAR scanners.

5. The medical imaging system of claim 4, wherein the plurality of LiDAR scanners are circumferentially disposed about the axis of rotation with each LiDAR scanner of the plurality of LiDAR scanners disposed at a different fixed angular position, and the plurality of LiDAR scanners are configured to acquire the data at the different angular positions at a same time while remaining stationary.

6. The medical imaging system of claim 1, wherein the LiDAR scanning system is configured to acquire the data prior to, during, and/or after the CT scan.

7. The medical imaging system of claim 1, wherein the processing circuitry is configured to utilize the 3D measurement in modifying scan acquisition parameters for the CT scan.

8. The medical imaging system of claim 1, wherein the processing circuitry is configured to utilize the 3D measurement in modifying reconstruction parameters used in generating a reconstructed image from CT scan data acquired during the CT scan.

9. The medical imaging system of claim 1, wherein the processing circuitry is configured to utilize the 3D measurement in modifying or optimizing patient positioning parameters for the CT scan.

10. A computed tomography (CT) imaging system, comprising:
    a gantry housing;
    a gantry coupled to the gantry housing and having a bore, rotatable about an axis of rotation;
    a table configured to move a subject to be imaged into and out of the bore of the gantry;
    a radiation source mounted on the gantry and configured to emit an X-ray beam;
    a detector configured to detect the X-ray beam emitted by the radiation source;
    a light detection and ranging (LiDAR) scanning system comprising:
        one or more LiDAR scanners configured to acquire data of the subject from different angular positions relative to the axis of rotation;
        a guide rail system configured to move the one or more LiDAR scanners relative to the gantry; and
    processing circuitry configured to receive the data acquired with the LiDAR scanning system, to generate a three-dimensional (3D) measurement of the subject, and to utilize the 3D measurement in a subsequent workflow process for a CT scan of the subject with the CT imaging system.

11. A medical imaging system, comprising:
    a computed tomography (CT) imaging system, comprising:

a gantry housing;
a gantry coupled to the gantry housing and having a bore, rotatable about an axis of rotation;
a table configured to move a subject to be imaged into and out of the bore of the gantry;
a radiation source mounted on the gantry and configured to emit an X-ray beam; and
a detector configured to detect the X-ray beam emitted by the radiation source;
a light detection and ranging (LiDAR) scanning system comprising one or more LiDAR scanners configured to acquire data of the subject from different angular positions relative to the axis of rotation, wherein the gantry housing comprises both a scan window and a LiDAR window disposed about the bore, and wherein the one or more LiDAR scanners are disposed beneath the LiDAR window between the scan window and a side of the gantry housing facing the table; and
processing circuitry configured to receive the data acquired with the LiDAR scanning system, to generate a three-dimensional (3D) measurement of the subject, and to utilize the 3D measurement in a subsequent workflow process for a CT scan of the subject with the CT imaging system.

12. The medical imaging system of claim 11, wherein the one or more LiDAR scanners are configured to rotate about the axis of rotation to acquire the data at the different angular positions.

* * * * *